United States Patent [19]

Husa et al.

[11] Patent Number: 5,281,590
[45] Date of Patent: Jan. 25, 1994

[54] 2-H AND 3-ALKOXY OR HYDROXY-8-SUBSTITUTED-DIBENZ[B,F]-[1,4]OXAZEPINE-10(11)-CARBOXYLIC ACID, SUBSTITUTED HYDRAZIDES FOR THE TREATMENT OF OSTEOPOROSIS

[75] Inventors: Robert K. Husa, Vernon Hills; E. Ann Hallinan, Evanston, both of Ill.; Marc Herin, Montignies sur Sambre; Michel Lesne, Kraainem, both of Belgium

[73] Assignee: G. D. Searle & Co., Chicago, Ill.

[21] Appl. No.: 939,262

[22] Filed: Sep. 2, 1992

Related U.S. Application Data

[62] Division of Ser. No. 695,630, May 3, 1991, Pat. No. 5,180,720.

[51] Int. Cl.$^5$ .................................................. A61K 31/55
[52] U.S. Cl. ............................................. 514/211; 540/547
[58] Field of Search ............................ 540/547; 514/211

[56] References Cited

U.S. PATENT DOCUMENTS

| | | | |
|---|---|---|---|
| 3,534,019 | 10/1970 | Coyne | 260/239 |
| 3,624,104 | 11/1971 | Cusic | 260/333 |
| 3,917,649 | 11/1975 | Mueller | 260/333 |
| 3,989,719 | 11/1976 | Mueller | 260/333 |
| 3,992,375 | 11/1976 | Mueller | 260/333 |
| 4,045,442 | 8/1977 | Mueller | 260/239.5 |
| 4,125,532 | 11/1978 | Mueller | 260/244.4 |
| 4,170,593 | 10/1979 | Mueller | 260/243.3 |
| 4,290,953 | 9/1981 | Koizumi | 260/333 |
| 4,559,336 | 12/1985 | Mueller | 514/211 |
| 4,559,337 | 12/1985 | Mueller | 514/211 |
| 4,614,617 | 9/1986 | Mueller | 540/547 |
| 4,704,386 | 11/1987 | Mueller | 514/211 |
| 5,182,272 | 1/1993 | Hallinan et al. | 514/80 |
| 5,212,169 | 5/1993 | Husa et al. | 514/211 |

FOREIGN PATENT DOCUMENTS

| | | |
|---|---|---|
| 0012385 | 6/1980 | European Pat. Off. . |
| 0193822 | 9/1986 | European Pat. Off. . |
| 0218077 | 4/1987 | European Pat. Off. . |
| 6700603 | 7/1967 | Netherlands . |
| WO92/19617 | 11/1992 | PCT Int'l Appl. ........ C07D 413/12 |
| 1170322 | 11/1969 | United Kingdom . |
| 1331892 | 9/1973 | United Kingdom . |
| 1522003 | 8/1978 | United Kingdom . |

OTHER PUBLICATIONS

*Drug Evaluations*, 6th ed (1986), Amer. Medical Assn., pp. 890–892.

*The Merck Manual*, 15th ed (1987), Merck and Co. Inc., pp. 1296–1297 and 2513.

A. Rakovska, et al., "Antagonistic Effect of SC-19220 on the Responses of Guinea-Pig Gastric Muscles to Prostaglandins $E_1$, $E_2$ and $F_2$," *Arch. Int. Pharmacodyn.*, 268, 59–69 (1984)–USA.

W. E. Coyne, et al., "Anticonvulsant Semicarbazides," *J. Med. Chem.*, 11(6), 1158–1160 (1968)–USA.

K. Gyires, et al., "The Use of the Writhing Test in Mice for Screening Different Types of Analgesics," *Arch. Int. Pharmacodyn.*, 267, 131–140 (1984) USA.

(List continued on next page.)

*Primary Examiner*—Emily Bernhardt
*Assistant Examiner*—Philip Datlow
*Attorney, Agent, or Firm*—Roberta L. Hastreiter; Roger A. Williams

[57] ABSTRACT

The present invention provides a method for treating osteoporosis in a mammal comprising administering to said mammal a therapeutically-effective amount of a compound of Formula I:

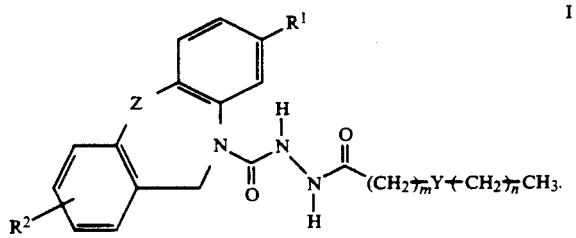

2 Claims, No Drawings

OTHER PUBLICATIONS

D. E. MacIntyre, et al., "Antagonism of Human Platelet Responses to Stimulatory and Inhibitory Prostaglandins," *Prog. Lipid. Res.* 20 (1–4), 453–9 (1981)–USA.

R. Gimet, et al., "Quantitative Determination of Polymorphic Forms in a Formulation Matrix Using the Near Infra-Red Reflectance Analysis Technique," *J. Pharmaceutical & Biomedical Analysis*, vol. 5, No. 3, 205–211 (1987)–USA.

J. H. Sanner, et al., "Structure–Activity Relationships of some Dibenzoxazepine Derivatives as Prostaglandin Antagonists," *Advances in the Biosciences*, 9, 139–148 (1972)–USA.

Drower, et al., "The Antiociceptive Effects of Prostaglandin Antagonists in the Rat" *European Journal of Pharmacology*, 133, 249–256 (1987)–Europe.

J. H. Sanner, "Dibenzoxazepine Hydrazides as Prostaglandin Antagonists," *Intra-Science Chem. Rept.*, vol. 6, No. 1, 1–9 (1972)–USA.

K. Nagarajan, et al., "Synthesis of 10,11-Dihydrodibenz[b,f][1,4]oxazepine Derivatives as Potential Anticonvulsants & Psychotropic Agents," *Indian Journal of Chemistry*, vol. 24B, 840–844 (1985)–India.

Lepore et al, Clinical and Experimental Rheumatology, 9 (Suppl. 6), pp. 33–35 (1991).

Waters et al, Acta Orthop Scand, 62(3), pp. 238–243 (1991).

Searle, PCT Application US92/08103 (unpublished) (1992).

T. Hagen, et al. United States Patent Application, 07/813,316, filed Dec. 20, 1991.

R. Husa, et al. United States Patent Application 07/869,563, filed Apr. 15, 1992.

E. Hallinan, et al. United States Patent Application 07/939,261, filed Sep. 2, 1992.

S. Nakajyo, et al., "Inhibitory Effect of Bassianolide, A Cyclodepsipeptide, on Drug-Induced Contractions of Isolates Smooth Muscle Preparations," *Japan. J. Pharmacol.*, 32, 55–64 (1982)–Japan.

A. Gomes, et al., "Pharmacodynamics of Venom of the Centipede *Scolopendra subspinipes dehaani*," Indian Journal of Experimental Biology, vol. 20, 615–618 (1982)–India.

A. Bennett, et al., "Antagonism of Prostanoid-Induced Contractions of Rat Gastric Fundus Muscle by SC-19220, Sodium Meclofenamate, Indomethacin or Trimethoquinol," *Br. J. Pharmac.*, 71, 169–175 (1980)–London.

C. A. Maggi, et al., "The Effect of SC-19220, a Prostaglandin Antagonist, on the Micturition Reflex in Rates," *European Journal of Pharmacology*, 152, 273–279 (1988)–Europe.

George, et al., "Antagonism of Alcohol Hypnosis by Blockade of Prostaglandin Synthesis and Activity: Genotype and Time Course Effects," *Pharmacology Biochemistry & Behavior*, vol. 19, 131–136 (1983)–USA.

2-H AND 3-ALKOXY OR HYDROXY-8-SUBSTITUTED-DIBENZ[B,F]-[1,4]OXAZEPINE-10(11)-CARBOXYLIC ACID, SUBSTITUTED HYDRAZIDES FOR THE TREATMENT OF OSTEOPOROSIS

This is a divisional application under 37 CFR §1.60 of co-pending application Ser. No. 07/695,630, filed on May 3, 1991, now U.S. Pat. No. 5,180,720.

BACKGROUND OF THE INVENTION (1) Field of the Invention

The present invention generally relates to compounds having pharmacological activity which are useful as pharmaceutical agents and, more particularly, as analgesic agents for the treatment of pain, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and medical methods of treating pain employing these compounds.

Analgesic compounds are agents which alleviate pain without causing a loss of consciousness and, thus, which are useful for treating pain and, often, for reducing inflammation.

The major classes of analgesic compounds include narcotic analgesics, or opiates, compounds which alleviate pain and induce sleep, and analgesic-antipyretic compounds, compounds which alleviate pain and reduce fever, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as With aspirin, allergic response, as with aspirin, and/or liver toxicity with extended use, as with acetaminophen.

The compounds of the present invention are neither opiates nor salicylates, and represent another class of compounds which are useful as analgesic agents.

(2) Description of the Related Art

U.S. Pat. Nos. 4,559,336 and 4,614,617 (a continuation-in-part of U.S. Pat. No. 4,559,336) disclose 8-chlorodibenz[b,f][1,4]-oxazepine-10(11H)-carboxylic acid, 2-(sulfinyl- and sulfonyl-containing acyl)hydrazides, and intermediates thereof.

U.S. Pat. No. 3,534,019 discloses hydrazides of dibenzoxazepine-, dibenzothiazepine- and dibenzodiazepine-carboxylic acids.

U.S. Pat. No. 3,624,104 discloses aralkanoyl derivatives of dibenzoxazepine-N-carboxylic acid hydrazide compounds.

U.S. Pat. No. 3,989,719 discloses N,N'-diacyl hydrazines.

U.S. Pat. Nos. 3,917,649 and 3,992,375 (a divisional of U.S. Pat. No. 3,917,649) disclose dibenzoxazepine N-carboxylic acid hydrazine compounds.

U.S. Pat. Nos. 4,045,442, 4,125,532 (a divisional of U.S. Pat. No. 4,045,442) and 4,170,593 (a divisional of U.S. Pat. No. 4,125,532) disclose 1-(substituted amino-)alkanoyl-2-(dibenzoxazepine-10-carbonyl)hydrazine compounds.

U.S. Pat. No. 4,559,337 discloses 8-chlorodibenz-[b,f][1,4]-oxazepine-10(11H)-carboxylic acid, 2-(alkoxy-containing acyl)hydrazide compounds.

GB 1 522 003 discloses 1-acyl-2-(8-chloro-10,11-dihydrodibenz[b,f][1,4]oxazepine-10-carbonyl)hydrazine compounds.

GB 1 331 892 discloses derivatives of dibenzoxazepine N-carboxylic acid hydrazides European Patent Application Publication No. 0 193 822 discloses 8-chlorodibenz[b,f][1,4]-oxazepine-10(11H)-carboxylic acid, 2-(thio-, sulfinyl- and sulfonyl-containing acyl)hydrazide compounds.

European patent Application publication No. 0 218 077 discloses 8-chlorodibenz[b,f][I,4]oxazepine-10(11H)-carboxylic acid, 2-[(substituted phenylsulfinyl)alkanoyl]hydrazide compounds and 8-chlorodibenz[b,f][1,4]oxazepine-10(11H)-carboxylic acid, 2-[(substituted phenylsulfonyl)alkanoyl]hydrazide compounds, and intermediates used in the preparation of these compounds.

Drower et al., "The Antiociceptive Effects of Prostaglandin Antagonists in the Rat," European Journal of Pharmacology, 133, 249–256 (1987), disclose the study of the antinociceptive properties of two competitive antagonists of prostaglandins of the E series, 8-chlorodibenz[b,f][1,4]-oxazepine-10(11H)-carboxylic acid, 2-acetylhydrazide and 8-chlorodibenz[b,f][1,4]-oxazepine-10(11H)-carboxylic acid, 2-(5-chloro-1-oxopentyl)-hydrazide .

J. H. Sanner, "Dibenzoxazepine Hydrazides as Prostaglandin Antagonists," Intra-Science Chem. Rept., 6(1), 1–9 (1972), describes experiments performed with two dibenzoxazepine derivative s designated SC-18637 and SC-19220, and shown below, and found that SC-18637 and SC-19220 inhibit the stimulant actions of prostaglandins on isolated smooth muscle preparations.

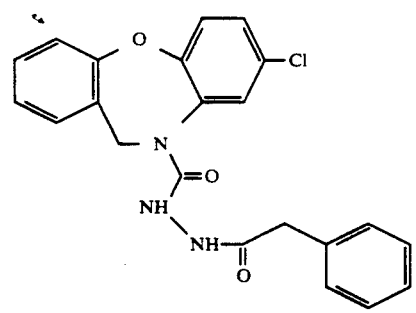

SC-18637

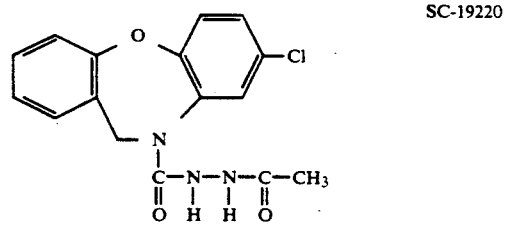

SC-19220

K. Nagarajan et al., "Synthesis of 10,11-Dihydrodibenz[b,f][1,4]oxazepine Derivatives as Potential Anticonvulsants & Psychotropic Agents," Indian Journal of Chemistry, 24B, 840–844 (1985), disclose the synthesis of acyl, carbamoyl and thiocarbamoyl derivatives of 10,11-dihydrodibenz[b,f][1,4]oxazepine, most of Which have either a nitro or an amino group at position-2, as analogues of carbamazepine, and the evaluation of these derivatives as anticonvulsants associated with neuroleptic activity.

Other art which relates to the present invention includes that which is discussed below.

D. E. MacIntyre et al., "Antagonism of Human Platelet Responses to Stimulatory and Inhibitory Prostaglandins," *Prog. Lipid. Res.*, 20(1–4), 453–9 (1981), disclose on Page 454, Lines 11–12, Page 458, Lines 43–44, and in Table 1, two dibenzoxazepine compounds designated SC-19220 and SC-25191, and shown above and below, respectively, which were employed in an investigation of the effects of prostaglandin antagonists on platelet responses to stimulatory and inhibitory prostaglandins.

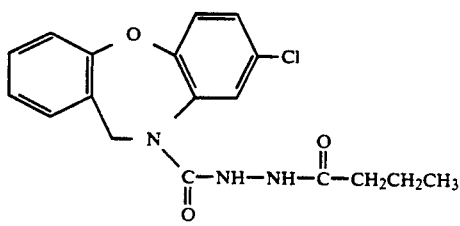

SC-25191

R. Gimet et al., "Quantitative Determination of Polymorphic Forms in a Formulation Matrix Using the Near Infra-Red Reflectance Analysis Technique," *J. Pharmaceutical & Biomedical Analysis*, 5(3), 205–211 (1987), disclose an analytical method for the determination of the polymorphic transformation of an active ingredient in a solid dosage form matrix, and discuss a compound designated SC-25469, and shown below, at Page 206, Lines 16–23.

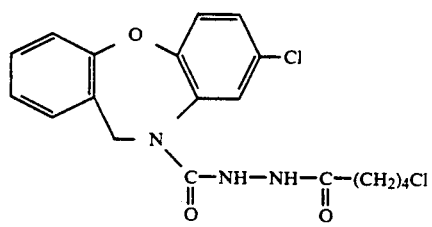

SC-25469

J. H. Sanner et al., "Structure-Activity Relationships of some Dibenzoxazepine Derivatives as prostaglandin Antagonists," *Advances in the Biosciences*, 9, 139–148 (1972), disclose tests for prostaglandin antagonism on isolated guinea-pig ileum and rat stomach fundus strips with the n-butanoyl, i-butanoyl and n-hexanoyl analogs of SC-19220 (see structure above) and, on Page 140, Lines 11–18, show the chemical structures of the compounds used in the study.

A. Rakovska et al., "Antagonistic Effect of SC-19220 on the Responses of Guinea-Pig Gastric Muscles to Prostaglandins $E_1$, $E_2$ and $F_2$," *Arch. int. Pharmacodyn*, 268, 59–69 (1984), disclose a study of the contractile responses of guinea-pig gastric muscles to SC-19220 (see structure above), and the prostaglandin-blocking activity and specificity of SC-19220 on these muscles.

W. E. Coyne et al., "Anticonvulsant Semicarbazides," *J. Med. Chem.*, 11(6), 1158–1160 (1968), disclose the investigation of the structure-activity relationship of the anticonvulsant activity of a series of semicarbazides which was synthesized from various tricyclic amines (see Table I, Page 1160).

K. Gyires et al., "The Use of the Writhing Test in Mice for Screening Different Types of Analgesics," *Arch. Int. Pharmacodyn*, 267 131–140 (1984), describe a comparison of the analgesic potency of some prostaglandin synthesis inhibitors, including SC-19220 (see structure above), and morphine using the writhing test. SC-19220 is discussed on page 133, Lines 10 and 14–16, in Table II (page 134), and on page 135, Lines 16–25, and Page 137, Lines 34–38.

A. Bennett et al., "Antagonism of Prostanoid-Induced Contractions of Rat Gastric Fundus Muscle by SC-19220, Sodium Meclofenamate, Indomethacin or Trimethoquinol," *Br. J. Pharmac*, 71, 169–175 (1980), disclose the study of the effects of several compounds, including SC-19220 (see structure above), on contractions of the rat stomach longitudinal muscle to several prostanoids. SC-19220 is discussed on page 175, Paragraph 1, Page 170, paragraph 4, in Table 1 and FIG. 2, on page 172, Paragraph 2, and on page 174, Paragraphs 1 and 2.

C. A. Maggi et al., "The Effect of SC-19220, a Prostaglandin Antagonist, on the Micturition Reflex in Rats," *European Journal of Pharmacology*, 152, 273–279 (1988), disclose a study in which SC-19220 (see structure above) is said to have increased the bladder capacity and reduced the voiding efficiency of micturition of urethane-anesthetized rats.

George et al., "Antagonism of Alcohol Hypnosis by Blockade of Prostaglandin Synthesis and Activity: Genotype and Time Course Effects," *Pharmacology Biochemistry & Behavior*, 19, 131–136 (1983), disclose a study of genetic and time-course factors of the effect of the antagonism of alcohol-induced behaviors of mice which have been pretreated with prostaglandin synthetase inhibitors and the effect of SC-19220 (see structure above) on ethanol sleep time.

S. Nakajyo et al., "Inhibitory Effect of Bassianolide, A Cyclodepsipeptide, on Drug-Induced Contractions of Isolates Smooth Muscle Preparations," Japan. *J. Pharmacol*, 32, 55–64 (1982), disclose a study of the effect of bassianolide on the contractile responses induced by various types of neurotransmitters and autacoids. SC-19220 (see structure above) was employed in this study and is discussed on page 57, Paragraph 1, in FIGS. 2 and 3, in Table 1, and on page 60, paragraph 1, Page 62, paragraph 3, and Page 63, Paragraph 2.

A. Gomes et al., "Pharmacodynamics of Venom of the Centipede *Scolopendra subspinipes dehaani*," *Indian Journal of Experimental Biology*, 20, 615–618 (1982), disclose an investigation of the pharmacodynamic actions of the venom of the tropical centipede S. subspinipes. SC-19220 (see structure above) was employed in this study and is discussed on page 615 (abstract), Page 616, Line 30, page 617, Lines 13–18, in FIGS. 4 and 5, and on page 618, Lines 23–26.

Each of the documents described hereinabove discloses compounds which are structurally different from the compounds of the present invention. Thus, the compounds of the present invention are structurally distinct from that Which has been described in the art.

Compounds of the present invention have been found to exhibit activity as prostaglandin $E_2$ antagonists.

SUMMARY OF THE INVENTION

The present invention provides compounds having a structure of Formula I:

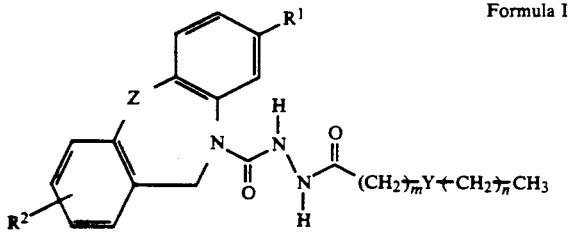

Formula I or a pharmaceutically-acceptable salt, ester or amide thereof, wherein:
R$_1$ is: hydrogen or halogen;
R$_2$ is: hydroxy or alkoxy;
Z is: oxygen, sulfur,

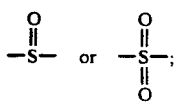

m is: an integer of from 1 to 4;
n is: an integer of from 1 to 4; and
Y is: sulfur,

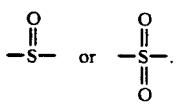

The present invention also provides pharmaceutical compositions which are pharmaceutically acceptable and Which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION

(1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The term "alkyl" as used herein means a saturated hydrocarbon radical having from one to six carbon atoms, which can be a straight or branched chain. Representative of such radicals are methyl, ethyl, iso-propyl, butyl, iso-butyl, sec-butyl, tert-butyl and the like.

The term "alkoxy" as used herein means an alkyl radical, as defined above, which has an oxygen atom attached thereto, and may be primary, secondary or tertiary. Representative alkoxy groups include methoxy, ethoxy, propoxy, iso-propoxy, sec-propoxy, tert-propoxy, butoxy, iso-butoxy, sec-butoxy, tert-butoxy and the like.

The term "analgesia" as used herein means the reduction, or absence, of sensibility to pain, designating particularly the relief of pain without loss of consciousness.

The term "animal" as used herein includes humans and animals.

The abbreviation "Boc" as used herein means t-butyloxycarbonyl.

The term "composition" as used herein means a product which results from the combining of more than one element or ingredient.

The abbreviation "DMF" as used herein means dimethyl formamide.

The phrase "EC$_{50}$ dose" as used herein means that dose of a compound or drug Which is necessary to elicit a 50% maximal biological response and, thus, which is necessary to elicit a 50% reduction in the contractions of guinea pig ileum segments in a prostaglandin antagonism assay.

The phrase "ED$_{50}$ dose" as used herein means that dose of a compound or drug which produced a biological effect, such as producing analgesia, in 50% of the animals to which the compound or drug was administered.

The abbreviation "Et" as used herein means ethyl (—CH$_2$CH$_3$).

The terms "halo" or "halogen" as used herein means chlorine (Cl), bromine (Br), fluorine (F) and/or iodine (I).

The term "heteroatom" as used herein means an atom of any element other than carbon or hydrogen.

The term "hydroxy" as used herein means an —OH group.

The abbreviation "HOAc" as used herein means acetic acid.

The abbreviation "i.g." as used herein means that a compound or drug was administered intragastrically, as defined below.

The term "intragastrically" as used herein means that a compound or drug was administered into the stomach.

The abbreviation "i.p." as used herein means that a compound or drug was administered intraperitoneally.

The abbreviation "Me" as used herein means methyl (—CH$_3$).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid or Which are prepared by reacting the free acid with a suitable base. Representative salts include the hydrochloride, hydrobromide, sulfate, bisulfate, acetate, valerate, oleate, palmitate, stearate, laurate, benzoate, lactate, phosphate, tosylate, citrate, maleate, fumarate, succinate, tartrate, napsylate, clavulanate and the like salts and alkali metal salts such as sodium and potassium and alkaline earth salts, such as calcium and magnesium.

The abbreviation "p.o." as used herein means that a compound or drug was administered orally.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The abbreviation "psi" as used herein means pounds per square inch.

The abbreviation "RaNi" as used herein means Raney nickel.

The abbreviation "s.c." as used herein means subcutaneously.

The abbreviation "THF" as used herein means tetrahydrofuran.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

(2) Description of Invention

In one aspect, the present invention provides compounds having a structure of Formula I, as described above, and pharmaceutically-acceptable salts, esters and amides thereof.

The compounds of the present invention comprise a class of substituted dibenzoxazepine compounds in which the 2-, 3-, 5-and/or 8-position, and/or the side chain, is substituted. Such compounds have been shown to exhibit activity as prostaglandin $E_2$ antagonists.

Specific compounds within the scope of the invention include, but are not limited to, the compounds discussed in the examples presented below, as well as their pharmaceutically-acceptable salts, esters, and amides.

contemplated equivalents of the compounds described in Formula I include compounds which otherwise correspond thereto, and which have the same general properties thereof, wherein one or more simple variations of substituents are made which do not adversely affect the efficacy of the compounds.

Certain compounds of this invention may exist in geometric or stereoisomeric forms. The present invention contemplates all such compounds, including cis- and trans- geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with an organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," *J. Pharm. Sci.*, 66:1–19 (1977).

In another aspect, the present invention provides pharmaceutically-acceptable compositions Which comprise a therapeutically-effective amount of one or more of the compounds of Formula 1, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal comprising administering a therapeutically-effective amount of a compound of Formula I, as described hereinabove, to the animal.

The most preferred embodiment of this invention is the compound which is shown and described in Example 4 below.

(3) Utility

Compounds of the present invention exhibit activity as prostaglandin $E_2$ antagonists (prostaglandin antagonists of the $E_2$ series).

Compounds within the present invention, and the pharmaceutical compositions comprising one or more of these compounds, are useful as analgesic agents for the elimination or amelioration of pain in animals.

In addition to treating pain, these compounds and compositions would be useful in treating convulsions, ischemia and other central nervous system disorders, as well as osteoporosis, dysmenorrhea, asthma, enuresis, arrhythmia and diarrhea, by virtue of their activity as prostaglandin $E_2$ antagonists.

(4) Methods of Preparation

In general, the compounds of the present invention may be prepared by the methods illustrated in the following general reaction scheme, or by modifications thereof, using readily-available starting materials, reagents and conventional synthesis procedures. Unless otherwise specified, the various substituents of the compounds and materials present in the general reaction scheme are defined in the same manner as they are defined above in Formula I.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

(5) Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may

GENERAL REACTION SCHEME

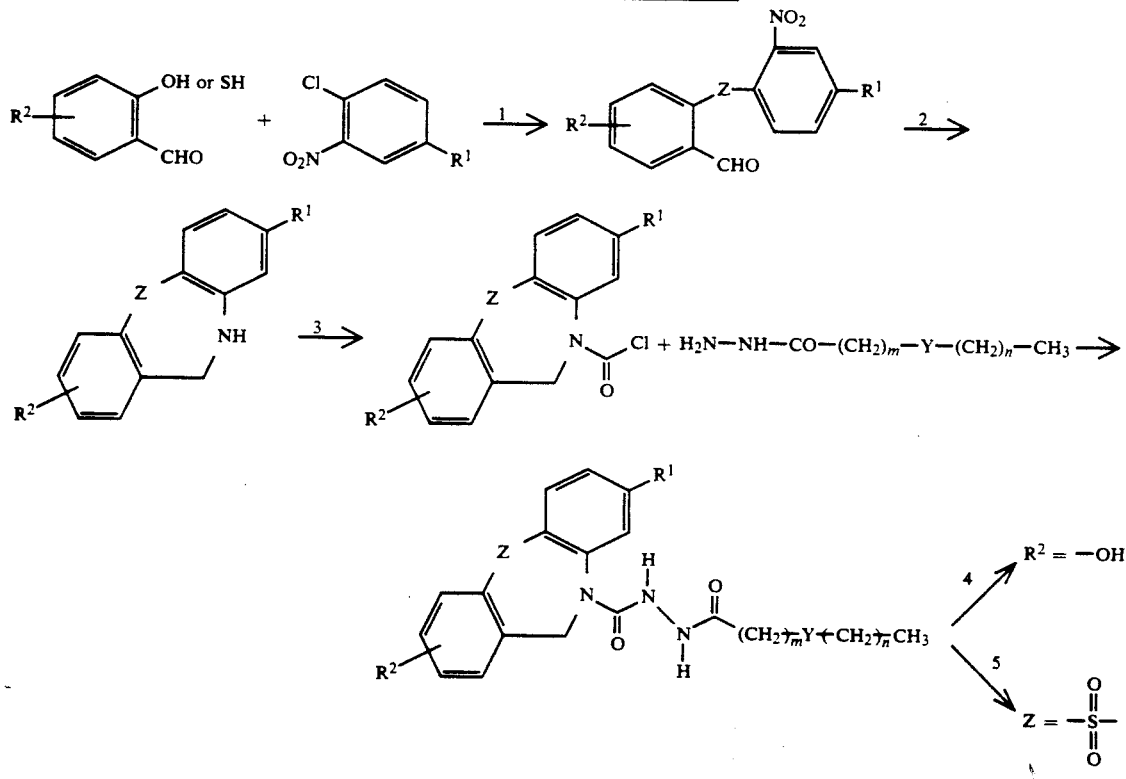

1 = NaH/DMF/85–90° C.
2 = RaNi/THF/5 psi H$_2$
3 = COCl$_2$/Et$_3$N/THF
4 = BBr$_3$/CH$_2$Cl$_2$ (This step is only done when it is desired to have R$^2$ be hydroxy.)
5 = H$_2$O$_2$/HOAc (This step is only done when it is desired to have Z be —SO$_2$—.)

The conditions for carrying out the individual steps in each of the general reaction schemes presented above are conventional, well-known, and capable of wide variation.

Other methods known in the art can also be used to synthesize the compounds of the present invention.

be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, dosage levels in the range of from about "0.001 mg to about 10 g, more preferably from about 1 mg to about 1000 mg, of active compound per kilogram of body weight per day are administered to a mammalian patient.

If desired, the effective daily dose of the active compound may be administered as two, three, four, five, six or more subdoses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred percent, this amount will range from about 1 percent to about ninety-nine percent of active ingredient, preferably from about 5 percent to about 70 percent most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (I) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I as described above), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, Will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

All starting materials used in the examples are commercially available. Most of the starting materials were obtained from Aldrich chemical co., Milwaukee, Wis.

All patents and publications referred to in the examples, and throughout the specification, are hereby incorporated herein by reference, without admission that such is prior art.

EXAMPLE 1

2-(4-chloro-2-nitrophenoxy)-5-methoxybenzaldehyde

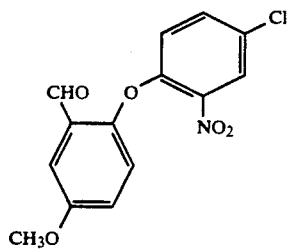

0.85 g of sodium hydride was added in portions to a stirred solution of 5.00 g of 2-hydroxy-5-methoxybenzaldehyde in 90 mL of N,N'-dimethylformamide under nitrogen. To the resulting milky, green mixture was added 5.74 g of 1,4-dichloro-2-nitrobenzene. The reaction was placed in an oil bath and stirred at 90° C. for 16 hours. The reaction was then evaporated in vacuo, and the residue partitioned between 75 mL of chloroform and 75 mL of 1N NaOH. The layers were separated and the aqueous layer was extracted With 75 mL of chloroform. The chloroform extracts were combined and washed with water (2×75 mL) and brine (75 mL), dried over magnesium sulfate, and evaporated in vacuo. The semi-solid residue was triturated with diethyl ether. The precipitated product was collected by filtration, washed with ether, and dried in vacuo to yield 5.96 g (64.8%) of product as a yellow solid. Melting Point: 127°–128° C.

EXAMPLE 2

8-chloro-10,11-dihydro-2-methoxydibenz-[b,f][1,4]oxazeoine

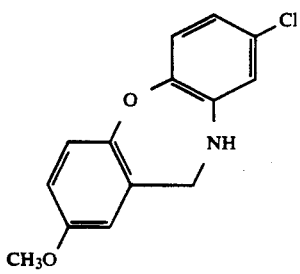

5.00 g of 2-(4-chloro-2-nitrophenoxy)-5-methoxybenzaldehyde, prepared as described above in Example 1, in 50 mL of tetrahydrofuran (THF) was shaken in a parr hydrogenator at 5 psi hydrogen with Raney nickel at 25° C. for 5 hours. The catalyst was filtered from the reaction and the solution evaporated in vacuo. The crude product was purified by column chromatography in the manner described by Still et al., "A Rapid Chromatographic Technique for Preparative Separations with Moderate Resolution," *J Org. Chem,* 43, 2923 (1978), through silica gel 60 using hexane:ethyl acetate (2:1) to yield 2.08 g (48.9%) of product as a white solid.

Melting Point: 111°-113° C.

EXAMPLE 3

8-chloro-2-methoxydibenz[b,f],1,4oxazeoine-10(11H)-carboxylic acid, 2-(3-(ethylsulfonyl)-1-oxopropyl]hydrazide

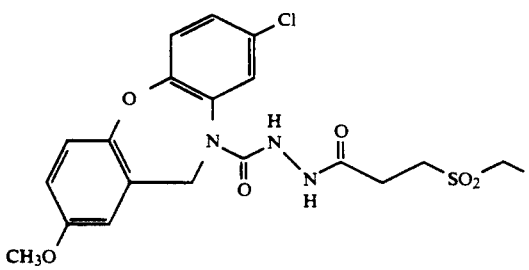

To a stirred solution of phosgene (1.93 M in 6.1 mL of toluene) in 30 mL of THF at approximately 5° C. (ice water bath) under nitrogen was added dropwise a solution of 8-chloro-10,11-dihydro-2-methoxydibenz-[b,f][1,4]oxazepine (1.6 g), prepared as described above in Example 2, and triethylamine (1.0 mL) in tetrahydrofuran (20 mL). The ice bath was removed and the reaction stirred at ambient temperature for 2 hours. The reaction was evaporated in vacuo, and to the residue Was added 2-[3-(ethylsulfonyl)-1-oxopropyl]hydrazide (1.21 g), triethylamine (1.0 mL) and toluene (35 mL). The reaction mixture was refluxed for 3 hours under nitrogen and then evaporated in vacuo. The residue was partitioned between ethyl acetate (150 mL) and 1N HCl (150 mL). The layers were separated and the aqueous layer was extracted once more with ethyl acetate (150 mL). The combined ethyl acetate extracts were washed with brine, dried over magnesium sulfate, and evaporated in vacuo. The residue Was crystallized from ethyl acetate:ethanol (95:5). Recrystallization from ethanol (3A) yielded 1.70 g (59.4%) of pure product as a white solid.

Melting Point: 173°-175° C.

EXAMPLE 4

8-chloro-2-hydroxydibenz [b,f][1,4]oxazepine-10(11H)-carboxylic acid, 2-[3-(ethylsulfonyl)-1-oxopropyl]hydrazide

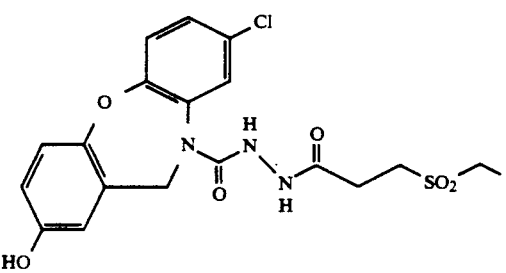

To a stirred suspension of 8-chloro-2-methoxydibenz-[b,f][1,4]oxazepine-10(11H)-carboxylic acid, 2-[3-(ethylsulfonyl)-1-oxopropyl]hydrazide (1.00 g), prepared in the manner described above in Example 3, in methylene chloride (5 mL) at approximately 5° C. (ice water bath) under nitrogen was added dropwise boron tribromide (1.0M in 6.7 mL of methylene chloride). The ice bath was removed and the reaction stirred at room temperature for 3 hours. The reaction was carefully quenched by the addition of 1N HCl, and poured into ethyl acetate (100 mL). The solution Was washed once with 1N HCl (100 mL). The 100 mL of 1N HCl wash was extracted With ethyl acetate (100 mL). The ethyl acetate solutions were combined and washed With 1N HCl, water and brine. Evaporation of the solution in vacuo resulted in a semi-solid residue. This was treated with 10 mL of ethanol (3A) and heated on a steam bath for several minutes to break up the solid. Upon cooling, the solidified product was collected by filtration. Recrystallization from ethanol (3A) yielded 0.44 g (45%) pure product as a white solid. Melting Point: 200°14 202° C.

EXAMPLE 5

2-(4-chloro-2-nitrophenoxy)-4-methoxvbenzaldehyde

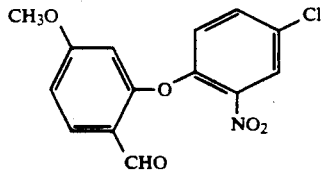

Sodium hydride (0.66 g) was added in portions to a stirred solution of 3.90 g of 2-hydroxy-4-methoxybenzaldehyde in N,N'-dimethylformamide (70 mL) under nitrogen. To the resulting milky, green mixture was added 1,4-dichloro-2-nitrobenzene (4.47 g). The reaction was placed in an oil bath and stirred at 90° C. for 16 hours. The reaction Was then evaporated and the residue partitioned between chloroform (75 mL) and 1N NaOH (50 mL). The layers were separated and the aqueous layer Was extracted with chloroform (75 mL). The chloroform extracts were combined and washed With Water (75 mL) and brine (75 mL), dried over magnesium sulfate, and evaporated in vacuo. The orange solid was recrystallized from ethyl acetate/isopropyl ether to yield 3.86 g (53.9%) of product as light yellow, shiny crystals.

Melting Point: 130°-131° C.

EXAMPLE 6

8-chloro-10,11-dihydro-3-methoxydibenz[b,f][1,4]oxazepine

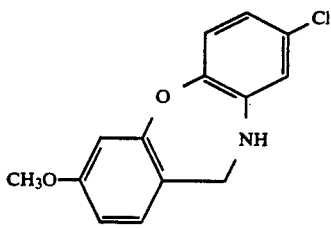

3.50 g of 2-(4-chloro-2-nitrophenoxy)-4-methoxybenzaldehyde, prepared as described above in Example 5, in tetrahydrofuran (THF) (35 mL) was shaken in a Parr hydrogenator at 5 psi hydrogen with Raney nickel at 25° C. for 6 hours. The catalyst was filtered from the reaction and the solution evaporated in vacuo. The crude product was chromatographed, as described above in Example 2, through silica gel 60 using hexane:ethyl acetate (2:1), and recrystallized from ethanol (3A) to yield 1.79 g (60.1%) of product as white crystals.

Melting Point: 113°-115° C.

EXAMPLE 7

8-chloro-3-methoxydibenz[b,f][1,4]oxazeoine-10(11H)-carboxylic acid,
2-[3-(ethylsulfonyl)-1-oxopropyl]hydrazide

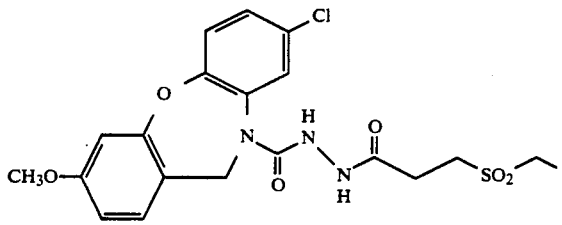

To a stirred solution of phosgene (1.93M in 6.1 mL of toluene) in tetrahydrofuran (30 mL) at approximately 5° C. (ice water bath) under nitrogen was added dropwise a solution of 1.69 g of 8-chloro-10,11-dihydro-3-methoxydibenz[b,f][]1,4]-oxazepine, prepared as described above in Example 6, and 1.0 mL of triethylamine in 20 mL of tetrahydrofuran. The ice bath was removed and the reaction stirred at ambient temperature for 2 hours. The reaction was evaporated in vacuo. and to the residue was added 2-[3-(ethylsulfonyl)-i-oxopropyl]hydrazide (1.21 g), triethylamine (1.0 mL), and toluene (35 mL). The reaction mixture was refluxed for 3.5 hours under nitrogen and then evaporated in vacuo. The residue was partitioned between ethyl acetate (150 mL) and 1N HCl (150 mL). The layers were separated and the aqueous layer was extracted once more with ethyl acetate (150 mL). The combined ethyl acetate extracts were Washed With water and brine, dried over magnesium sulfate, and evaporated in vacuo. The residue was chromatographed, as described above in Example 2, through silica gel 60 using ethyl acetate:ethanol (3A) (95:5) to yield 2.09 g (73.0%) of product as a solidified foam.

EXAMPLE 8

8-chloro-3-hydroxydibenz[b,f]1,4oxazepine-10(11H)-carboxylic acid,
2-[3-(ethylsulfonyl)-1-oxopropyl]hydrazide

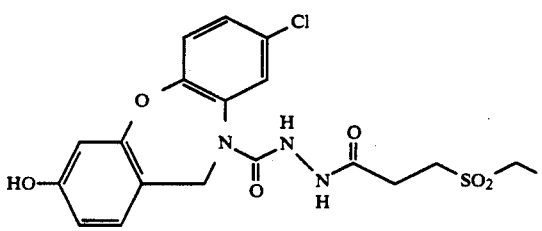

To a stirred solution of boron tribromide (1.0M in 7.3 mL of methylene chloride) at approximately 5° C. (ice water bath) under nitrogen was added dropwise 1.09 g of 8-chloro-3-methoxydibenz[b,f][1,4]oxazepine-10(11H)-carboxylic acid, 2-[3-(ethylsulfonyl)-1-oxopropyl]hydrazide, prepared as described above in Example 7, in 5 mL of methylene chloride. The ice bath was removed and the reaction stirred at room temperature for 3 hours. The reaction was carefully quenched by the addition of 10 mL of 1N HCl, and poured into 150 mL of ethyl acetate. The solution was washed with 150 mL of 1N HCl and brine, dried over magnesium sulfate, and evaporated in vacuo to a greenish residue. This was treated with 10 mL of ethanol (3A), and the resulting solid was collected by filtration. Recrystallization from ethanol (3A) yielded 0.58 g (54.9%) pure product as a white solid.

Melting Point: 217°-218° C.

The identity and purity of the products synthesized in Examples 3, 4, 7 and 8 were confirmed by $^1$H NMR, $^{13}$C NMR, microanalysis, and high performance liquid chromatography (HPLC). The results of these analyses are presented in Table 1 below.

TABLE I

| Example Number | Elemental Analysis | | | | | | HPLC % | Melting Point °C. |
|---|---|---|---|---|---|---|---|---|
| | % C | | % H | | % N | | | |
| | Calculated | Found | Calculated | Found | Calculated | Found | | |
| Example 3 | 51.34 | 51.28 | 4.47 | 4.66 | 8.98 | 8.93 | 99.5 | 173-175 |
| Example 4 | 50.28 | 50.29 | 4.44 | 4.47 | 9.26 | 9.23 | 99.1 | 200-202 |
| Example 7 | 51.34 | 51.31 | 4.47 | 4.78 | 8.98 | 8.75 | 99.6 | * |
| Example 8 | 50.28 | 50.11 | 4.44 | 4.38 | 9.26 | 9.13 | 99.6 | 217-218 |

*No melting point (isolated as a solidified foam).

The foregoing examples are provided to enable one of ordinary skill in the art to practice the present invention. These examples are merely illustrative, however, and should not be read as limiting the scope of the invention as it is claimed in the appended claims.

(7) Assays

(a) Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., *Arch. int. Pharmacodyn*, 267, 131–140 (1984); C. Vander Wende et al., *Fed. Proc.*, 15, 494 (1956); Koster et al., *Fed. Proc.*, 18, 412 (1959); and Witken et al., *J. Pharmacol. exp. Ther.*, 133, 400–408 (1961).] Chemicals which may be used to induce this pain include phenylbenzoquinone (pBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table 2 below.

Charles River male albino mice, weighing 20 to 30 grams were used in this assay.

Thirty minutes after subcutaneous or intragastric administration to ten mice of 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to have produced analgesia in a mouse if, in accordance with the conditions set forth above, and under the test criteria employed for this assay, after the administration of 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology*, 8, 191 (1974).

The results for the particular compounds of the present invention analyzed in this assay, and discussed in the examples identified below which correspond thereto are presented in Table 2 below.

The standard initial screening dose of a test compound employed in this assay was 30 mg per kilogram of body weight for both routes of administration. If this initial screening dose of the test compound produced analgesia in seven out of ten mice, then the effect of additional doses of the test compound on the writhing response was evaluated, and then the $ED_{50}$ dose was generally calculated. (The slopes of the dose-response curves for all test compounds analyzed were compared as described by Tallarida and Murray, *Manual of Pharmacologic Calculations*, Page 11 (Springer Verlag, N.Y., 1981)).

All $ED_{50}$ doses calculated are also presented in Table 2. The rank order of potency of the more potent compounds of the present invention tested in the Writhing Assay was (referring to the particular example which describes the preparation of the compound): Example 4 > Example 8 > Example 7 > Example 3. Thus, 8-chloro-2-hydroxydibenz-[b,f][1,4]oxazepine-10(11H)-carboxylic acid, 2-[3-(ethylsulfonyl)-1-oxopropyl]hydrazide (Example 4) was determined to be the most potent compound of the invention tested in this assay and, thus, is the most preferred compound of the present invention.

(b) Prostaglandin (PGE) Antagonism Assay

In order to determine the effectiveness of compounds of the invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound antagonizes prostaglandin $E_2$.

Male albino guinea pigs weighing 200 to 500 grams were sacrificed by cervical dislocation.

The ileums were then quickly removed from the guinea pigs and placed in a modified Tyrode solution, a solution which is known to those of skill in the art, containing one-half of the usual amount of magnesium ions.

Segments of ileum about 2 cm long were then cut and mounted in a 10-mL tissue bath containing the modified Tyrode solution. The solution was maintained at 37° C. and aerated with a gaseous mixture of 95% oxygen and 5% carbon dioxide.

Submaximal contractions of the ileum segments were then generated by injecting prostaglandin $E_2$ into the bath, and detected isotonically. Data for a control prostaglandin $E_2$ dose response curve plotting concentration of prostaglandin $E_2$ versus number of contractions generated was then obtained by experimentally adjusting the dose of the prostaglandin $E_2$ being injected into the tissue bath, in a manner known by those of skill in the art.

Solutions or suspensions containing an initial amount of a test compound in modified Tyrode solution ("test solutions/suspensions") were then separately substituted for the tissue bath. Each test solution/suspension was then kept in constant contact with the ileum tissue, except for brief periods to drain the bath in preparation for rinsing with fresh test solution/suspension. Different doses of prostaglandin $E_2$ were again injected into the test solutions/suspensions.

A second prostaglandin $E_2$ dose response curve was then generated for $PGE_2$ in the presence of a test compound.

A dose ratio of $Ec_{50}$ doses (that dose of a compound or drug which is necessary to elicit a 50% maximal biological response and, thus, which is necessary to elicit a 50% reduction in the contractions of the guinea pig ileum segments in this assay) was then calculated from the results of each test in a manner known by those of skill in the art. A concentration of the test compound was determined to be "active" if it produced a dose ratio significantly greater than that obtained in a series of blank treatments. Duplicate tests were conducted on each concentration of a test compound.

If the initial concentration of a test compound was determined to be "active," then varying concentrations of the test compound were then assayed.

The pA$_2$ value (a statistical constant which is a common measure of expressing the potency of a particular drug as a competitive antagonist) was then calculated for the test compound by schild plot calculations, as described by H. O. Schild, "pA, A New Scale for the Measurement of Drug Antagonism," *Br. J. Pharmacol,* 2, 189 (1947), according to the following mathematical formula:

$$pA_2 = -\log[\text{Test Compound}]$$

to quantitate the effectiveness of the test compound as a prostaglandin E$_2$ antagonist. The higher the value calculated for pA$_b$ 2, the more potent a particular compound is as a prostaglandin E$_2$ antagonist.

The results of this prostaglandin antagonism assay are also presented in Table 2 below. The results presented in Table 2 show that the compound of the present invention shown and described in Example 4 exhibits activity as a prostaglandin E$_2$ antagonist.

TABLE 2

| | Data Generated from the Assays | | |
|---|---|---|---|
| | PBQ WRITHING ASSAY (30 mg/kg) (ED$_{50}$ (mpk)) | | PGE ANTAGONISM IN GUINEA PIG ILEUM |
| Example Number | S.C. | I.G. | (pA$_2$) |
| Example 3 | * | * | Not Yet Tested |
| Example 4 | Active | Active (12.6) | Active (5.4) |
| Example 7 | * | Active | Not Yet Tested |
| Example 8 | Active | Active | Not Yet Tested |

*Indicates that, in accordance with the particular conditions set forth above for the Writhing Assay, and under the test criteria employed for that assay, after the administration of an initial screening dosage of 30 mg per kilogram of the compound, the number of writhes elicited by a mouse injected with PBQ was not equal to, or less than, one-half the median number of writhes recorded for the saline-treated control group of mice that day.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A method for treating osteoporosis in a mammal comprising administering to said mammal a therapeutically-effective amount of a compound having the formula:

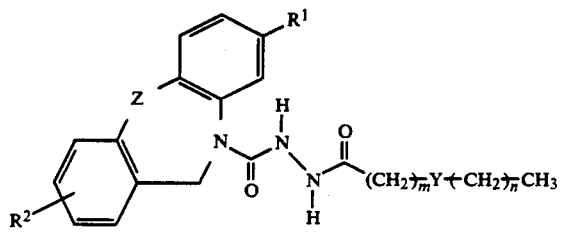

or a pharmaceutically-acceptable salt thereof, wherein:
R$^1$ is: hydrogen or halogen;
R$^2$ is: hydroxy or alkoxy;
Z is: oxygen, sulfur,

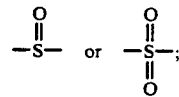

m is: an integer of from 1 to 4;
n is: an integer of from 1 to 4; and
Y is: sulfur,

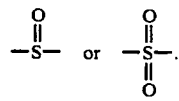

2. The method of claim 1, wherein the compoudn is selected from the group consisting of:
8-chloro-2-methoxydibenz[b,f][1,4]oxazepine-10(11H)-carboxylic acid, 2-[3-(ethylsulfonyl)-1-oxopropyl]hydrazide;
8-chloro-2-hydroxydibenz[b,f][1,4]oxazepine-10(11H)-carboxylic acid, 2-[3-(ethylsulfonyl)-1-oxopropyl]hydrazide;
8-chloro-3-methoxydibenz[b,f][1,4]oxazepine-10(11H)-carboxylic acid, 2-[3-(ethylsulfonyl)-1-oxopropyl]hydrazide; or
8-chloro-3-hydroxydibenz[b,f][1,4]oxazepine-10(11H)-carboxylic acid, 2-[3-(ethylsulfonyl)-1-oxopropyl]hydrazide.

* * * * *

UNITED STATES PATENT AND TRADEMARK OFFICE
CERTIFICATE OF CORRECTION

PATENT NO. : 5,281,590

DATED : January 25, 1994

INVENTOR(S) : Husa, et al.

It is certified that error appears in the above-identified patent and that said Letters Patent is hereby corrected as shown below:

On the cover page the first part of the title reading "2-H AND 3-ALKOXY" should read -- 2- AND 3-ALKOXY --.

Column 1, line 1, the first part of the title reading "2-H AND 3-ALKOXY" should read -- 2- AND 3-ALKOXY --.

Column 1, line 41, reading "as With" should read -- as with --.

Column 2, line 8, reading "hydrazides" should read -- hydrazides. --.

Column 2, line 13, reading "European patent" should read -- European Patent --.

Column 2, line 14, reading "[I,4]" should read -- [1,4] --.

Column 2, line 33, reading "derivative s" should read -- derivatives --.

Column 2, line 67, reading "Which have" should read -- which have --.

Column 3, line 5, reading "D.E. MacIntyre" should read -- D.E. MacIntyre --.

Column 3, line 27, reading "lnfra-Red" should read -- Infra-Red --.

UNITED STATES PATENT AND TRADEMARK OFFICE
CERTIFICATE OF CORRECTION

PATENT NO. : 5,281,590

DATED : January 25, 1994

INVENTOR(S) : Husa, et al.

It is certified that error appears in the above-identified patent and that said Letters Patent is hereby corrected as shown below:

Column 3, line 46, reading "as prostaglandin" should read -- as Prostaglandin --.

Column 4, line 1, reading "267 131-140" should read -- 267, 131-140 --.

Column 4, line 61, reading "Which has" should read -- which has --.

Column 5, line 35, reading "and Which" should read -- and which --.

Column 6, line 11, reading "drug Which" should read -- drug which --.

Column 6, line 25, reading "(1)." should read -- (I). --.

Column 7, line 20, reading "Which are" should read -- which are --.

Column 7, line 66, reading "contemplated" should read -- Contemplated --.

Column 8, line 35, reading "(1977)." should read -- (1977).) --.

Column 8, line 37, reading "Which" should read -- which --.

UNITED STATES PATENT AND TRADEMARK OFFICE
CERTIFICATE OF CORRECTION

PATENT NO. : 5,281,590

DATED : January 25, 1994

INVENTOR(S) : Husa, et al.

It is certified that error appears in the above-identified patent and that said Letters Patent is hereby corrected as shown below:

Column 8, line 39, reading "Formula 1," should read -- Formula I, --.

Column 11, line 1, reading "parenterally" should read -- parenterally, --.

Column 11, line 44, reading ""0.001 mg" should read -- 0.001 mg --.

Column 12, line 58, reading "(I) fillers" should read -- (1) fillers --.

Column 14, line 12, reading "Will melt" should read -- will melt --.

Column 16, line 29, reading "Aldrich chemical co.," should read -- Aldrich Chemical Co., --.

Column 16, line 60, reading "With 75 mL" should read -- with 75 mL --.

Column 17, line 3, reading "oxazeoine" should read -- oxazepine --.

Column 17, line 20, reading "parr" should read -- Parr --.

Column 17, line 27, reading "J Org. Chem," should read -- J. Org. Chem, --.

UNITED STATES PATENT AND TRADEMARK OFFICE
CERTIFICATE OF CORRECTION

PATENT NO. : 5,281,590          Page 4 of 6
DATED      : January 25, 1994
INVENTOR(S): Husa, et al.

It is certified that error appears in the above-indentified patent and that said Letters Patent is hereby corrected as shown below:

Column 17, line 33, reading "[b,f],1,4" should read -- [b,f][1,4] --.

Column 17, line 35, reading "2-(3-" should read -- 2-[3- --.

Column 17, line 58, reading "Was added" should read -- was added --.

Column 17, line 67, reading "residue Was" should read -- residue was --.

Column 18, line 32, reading "Was washed" should read -- was washed --.

Column 18, line 34, reading "With ethyl" should read -- with ethyl --.

Column 18, line 35, reading "With 1N" should read -- with 1N --.

Column 18, line 42, reading "200°14 202°" should read -- 200°-202° --.

Column 18, line 45, reading " methoxvbenzaldehyde" should read -- methoxybenzaldehyde --.

Column 18, line 61, reading "Was then" should read -- was then --.

UNITED STATES PATENT AND TRADEMARK OFFICE
CERTIFICATE OF CORRECTION

PATENT NO. : 5,281,590
DATED : January 25, 1994
INVENTOR(S) : Husa, et al.

It is certified that error appears in the above-identified patent and that said Letters Patent is hereby corrected as shown below:

Column 18, line 64, reading "Was extracted" should read -- was extracted --.

Column 18, line 66, reading "With Water" should read -- with water --.

Column 19, line 33, reading "oxazeoine" should read -- oxazepine --.

Column 19, line 65, reading "in vacuo." should read -- in vacuo, --.

Column 19, line 66, reading "-i-oxopropyl" should read -- 1-oxopropyl --.

Column 20, line 6, reading "Washed With" should read -- washed with --.

Column 20, line 14, reading "[b,f]1,4" should read -- [b,f][1,4] --.

Column 20, line 28, reading "(I.OM" should read -- (1.OM --.

Column 20, line 50, reading "Table 1 below." should read -- Table I below. --.

Column 21, line 14, reading "(pBQ)" should read -- (PBQ) --.

Column 22, line 15, reading "Prostaclandin" should read -- Prostaglandin --.

UNITED STATES PATENT AND TRADEMARK OFFICE
CERTIFICATE OF CORRECTION

PATENT NO. : 5,281,590          Page 6 of 6
DATED : January 25, 1994
INVENTOR(S) : Husa, et al.

It is certified that error appears in the above-indentified patent and that said Letters Patent is hereby corrected as shown below:

Column 22, line 58, reading "Ec$_{50}$" should read -- EC$_{50}$ --.

Column 23, line 17, reading "pA$_b$ $_2$," should read -- pA$_2$, --.

Column 24, line 43, reading "compoudn" should read -- compound --.

Signed and Sealed this

Nineteenth Day of September, 1995

Attest:

BRUCE LEHMAN

Attesting Officer          Commissioner of Patents and Trademarks